United States Patent
Altschul et al.

(10) Patent No.: US 10,441,316 B2
(45) Date of Patent: Oct. 15, 2019

(54) INTRADERMAL APPLICATOR/ANALYTE SENSOR PLACEMENT USING FLUORESCENCE

(71) Applicant: POP TEST LLC, Cliffside Park, NJ (US)

(72) Inventors: Randice Lisa Altschul, Cliffside Park, NJ (US); Neil David Theise, New York, NY (US); Razvan Andrei Ene, Vimercate (IT); Myron Rapkin, Indianapolis, IN (US); Rebecca O'Brien, Shell Knob, MO (US)

(73) Assignee: Pop Test LLC, Cliffside Park, NJ (US)

( * ) Notice: Subject to any disclaimer, the term of this patent is extended or adjusted under 35 U.S.C. 154(b) by 0 days.

(21) Appl. No.: 15/758,531

(22) PCT Filed: Sep. 9, 2016

(86) PCT No.: PCT/US2016/050893
§ 371 (c)(1),
(2) Date: Mar. 8, 2018

(87) PCT Pub. No.: WO2017/044702
PCT Pub. Date: Mar. 16, 2017

(65) Prior Publication Data
US 2018/0256208 A1 Sep. 13, 2018

Related U.S. Application Data (60) Provisional application No. 62/217,347, filed on Sep. 11, 2015.

(51) Int. Cl.
*A61B 5/145* (2006.01)
*A61B 17/34* (2006.01)
(Continued)

(52) U.S. Cl.
CPC ........ *A61B 17/3468* (2013.01); *A61B 5/0071* (2013.01); *A61B 5/0077* (2013.01);
(Continued)

(58) Field of Classification Search
CPC ................................................. A61B 5/0071
See application file for complete search history.

(56) References Cited

U.S. PATENT DOCUMENTS

| | | |
|---|---|---|
| 4,100,401 A | 7/1978 | Tutt et al. |
| 4,159,416 A | 6/1979 | Brejnik et al. |

(Continued)

FOREIGN PATENT DOCUMENTS

EP 2335587 B1 2/2014

OTHER PUBLICATIONS

Murakami et al.; "A miniature confocal optical microscope with MEMS gimbal scanner"; Transducers '03; The 12th International Conference on Solid State Sensors, Actuators and Microsystems; Jun. 8-12, 2003; pp. 587-590; IEEE.*

(Continued)

*Primary Examiner* — Luther Behringer
(74) *Attorney, Agent, or Firm* — Caesar Rivise, PC (57) ABSTRACT

The present invention provides for a method and apparatus for inserting and using dermal interstitial sensors in, for example, an analyte monitoring system. The present invention permits the proper positioning of a cannula tip and/or sensor(s) within the reticular dermis.

5 Claims, 2 Drawing Sheets

(51) Int. Cl.

| | | |
|---|---|---|
| *A61M 37/00* | (2006.01) | |
| *A61B 10/00* | (2006.01) | |
| *A61B 10/02* | (2006.01) | |
| *A61B 34/20* | (2016.01) | |
| *A61B 90/20* | (2016.01) | |
| *A61B 5/00* | (2006.01) | |
| *A61B 5/07* | (2006.01) | |
| *A61B 90/30* | (2016.01) | |
| *A61B 90/00* | (2016.01) | |

(52) U.S. Cl.
CPC ............ *A61B 5/076* (2013.01); *A61B 5/1451* (2013.01); *A61B 5/14503* (2013.01); *A61B 5/14532* (2013.01); *A61B 5/4845* (2013.01); *A61B 5/6861* (2013.01); *A61B 5/742* (2013.01); *A61B 10/0045* (2013.01); *A61B 10/0233* (2013.01); *A61B 17/34* (2013.01); *A61B 17/3403* (2013.01); *A61B 34/20* (2016.02); *A61B 90/20* (2016.02); *A61M 37/00* (2013.01); *A61M 37/0069* (2013.01); *A61B 5/14546* (2013.01); *A61B 2010/008* (2013.01); *A61B 2017/3407* (2013.01); *A61B 2034/2057* (2016.02); *A61B 2090/304* (2016.02); *A61B 2090/395* (2016.02); *A61B 2090/3925* (2016.02); *A61B 2090/3933* (2016.02); *A61B 2090/3941* (2016.02); *A61B 2090/3954* (2016.02); *A61B 2090/3966* (2016.02); *A61B 2560/066* (2013.01)

(56) References Cited

U.S. PATENT DOCUMENTS

| | | | |
|---|---|---|---|
| 4,436,094 | A | 3/1984 | Cerami |
| 4,953,552 | A | 9/1990 | DeMarzo |
| 5,497,772 | A | 3/1996 | Schulman et al. |
| 5,522,394 | A | 6/1996 | Zurbuegg |
| 5,589,932 | A | 12/1996 | Garcia-Rubio et al. |
| 5,815,954 | A | 10/1998 | Huang |
| 5,873,835 | A | 2/1999 | Hastings et al. |
| 6,111,520 | A | 8/2000 | Allen et al. |
| 6,278,379 | B1 | 8/2001 | Allen et al. |
| 6,304,766 | B1 | 10/2001 | Colvin |
| 6,409,674 | B1 | 6/2002 | Brockway et al. |
| 6,475,639 | B2 | 11/2002 | Shahinpoor et al. |
| 6,517,482 | B1 | 2/2003 | Elden et al. |
| 6,675,030 | B2 | 1/2004 | Ciurczak et al. |
| 6,802,811 | B1 | 10/2004 | Slepian |
| 6,836,678 | B2 | 12/2004 | Tu |
| 6,855,115 | B2 | 2/2005 | Fonesca et al. |
| 6,954,662 | B2 | 10/2005 | Freger et al. |
| 7,027,134 | B1 | 4/2006 | Garcia-Rubio et al. |
| 7,125,382 | B2 | 10/2006 | Zhou et al. |
| 7,184,810 | B2 | 2/2007 | Caduff et al. |
| 7,299,080 | B2 | 11/2007 | Acosta et al. |
| 7,334,472 | B2 | 2/2008 | Seo et al. |
| 7,966,060 | B2 * | 6/2011 | Smit .................... A61B 5/0059 600/310 |
| 8,938,297 | B2 | 1/2015 | Greiner et al. |
| 2004/0186363 | A1 * | 9/2004 | Smit .................... A61B 5/0059 600/317 |
| 2005/0277839 | A1 | 12/2005 | Alderman et al. |
| 2006/0020191 | A1 * | 1/2006 | Brister ................ A61B 5/0002 600/345 |
| 2009/0240113 | A1 | 9/2009 | Heckerman |
| 2010/0049004 | A1 | 2/2010 | Edman et al. |
| 2010/0049021 | A1 | 2/2010 | Jina et al. |
| 2010/0081910 | A1 | 4/2010 | Brister et al. |
| 2010/0217212 | A1 | 8/2010 | Eppstein |
| 2011/0230835 | A1 | 9/2011 | Müller et al. |
| 2013/0072856 | A1 | 3/2013 | Frankhouser et al. |
| 2013/0310680 | A1 * | 11/2013 | Werahera ............ A61B 5/0035 600/411 |
| 2015/0148685 | A1 * | 5/2015 | Baym .................... A61B 5/445 600/476 |

OTHER PUBLICATIONS

PCT Written Opinion of PCT/US2016/050893 dated Mar. 22, 2018.
International Search Report of PCT/US2016/050893 dated Dec. 29, 2016.
Mattley, Y. D., et al. "Blood characterization using UV/vis spectroscopy." In Advances in Fluorescence Sensing Technology II, vol. 2388, pp. 462-471. International Society for Optics and Photonics, 1995.
Lakowicz, J. R. "Advances in fluorescence sensing technology II." In Proc. SPIE, vol. 2388, pp. 159-170. 1995.
Hoenes, J. et al. "The technology behind glucose meters: test strips." Diabetes Technology & Therapeutics 10, No. S1 (2008): S-10, Abstract.
Hermanides, J., and J. H. DeVries. "Sense and nonsense in sensors." Diabetologia 53, No. 4 (2010): 593-596.
Moore, B. "The potential use of radio frequency identification devices for active monitoring of blood glucose levels." Journal of diabetes science and technology 3, No. 1 (2009): 180-183.
Nielsen, J. et al. "Clinical evaluation of a transcutaneous interrogated fluorescence lifetime-based microsensor for continuous glucose reading." Journal of diabetes science and technology 3, No. 1 (2009): 98-109.
Li, S. et al. "Development of novel glucose sensing fluids with potential application to microelectromechanical systems-based continuous glucose monitoring." Journal of diabetes science and technology 2, No. 6 (2008): 1066-1074.
Mok, W., and Li, Y. "Recent progress in nucleic acid aptamer-based biosensors and bioassays." Sensors 8, No. 11 (2008): 7050-7084.
Snow, E S. et al. "Chemical detection with a single-walled carbon nanotube capacitor." Science 307, No. 5717 (2005): 1942-1945.
Hagleitner, C. et al. "Smart single-chip gas sensor microsystem." Nature 414, No. 6861 (2001): 293, Abstract.
"Electroacupuncture." Acupuncture Today—The Leading Provider of Acupuncture and Traditional Chinese Medicine News and Research Information in the World—TCM—Find an Acupuncturist. Accessed Mar. 4, 2019. https://www.acupuncturetoday.com/abc/electroacupuncture.php.
Supplementary European Search Report for corresponding European Patent Application No. EP16845095 dated Aug. 26, 2019.

* cited by examiner

INTRADERMAL APPLICATOR/ANALYTE SENSOR PLACEMENT USING FLUORESCENCE

CROSS-REFERENCE TO RELATED APPLICATIONS

This application claims benefit under 35 USC 119(e) to U.S. Provisional Application No. 62/217,347 filed Sep. 11, 2015, the contents of which are incorporated by reference herein in their entirety.

BACKGROUND OF THE INVENTION

The present invention provides for a method and apparatus for inserting and using dermal interstitial sensors in, for example, an analyte monitoring system.

The dermis, the second layer of the skin, is usually described as a densely compacted layer of fibroconnective tissue through which course small branches of arteries, veins and lymphatic vessels, as well as nerves. Recent data obtained by correlation of histologic findings with in vivo microscopy reveal that this appearance of densely compacted fibroconnective tissue is artefactual; the living dermis is a cavernous interstitial sinus supported and defined by an extensive lattice of thick collagen bundles lined on one side by a CD34+ cell without endothelial ultrastrucure: perhaps a modified endothelial cell, a fibroblast, and/or mesenchymal stem cell. The interstitial fluid flowing in this space in living tissue is derived from serum and may be considered pre-lymph. Molecules in the serum reach the interstitial fluid within minutes of change, as demonstrated by intravascular infusion of fluorescein whereby, within minutes, in vivo microscopy reveals fluorescence of the dermal interstitial sinus.

This lymph, imprecisely termed "interstitial fluid", contains biomolecules, such as proteins, glycoproteins, sugars, lipids, etc, as they are found in the blood. Indwelling sensors that can detect such molecules are known, in particular glucose sensors that are inserted into the skin. However, inventors and users of these devices are imprecise in their identification of the "interstitial fluid" that is being monitored and of the precise location and anatomy of device insertion. These devices often decline in signal integrity over time and also have skin irritative effects that require regular replacement, perhaps due to the invasion of deeper tissues generating tissue reactions. The lack of understanding of the anatomy of the dermal lymphatic sinus has led to such imprecisions which this present invention alleviates.

This present invention describes a method of placement of such a sensor so that it lies entirely within the dermal lymphatic sinus or reticular dermis, providing consistent and maximal exposure to lymph. The device would be positioned by first inserting a trocar at a shallow angle into the dermal lymphatic sinus or reticular dermis, removal of the obturator component leaving the hollow cannula. Lymph draining from the cannula confirms correct placement and then the sensor device is slipped through the cannula and cannula is removed, leaving the device in place, fully within the dermal lymphatic sinus or reticular dermis. This device may be connected to:

An external device for registering and transmission of data from the sensor to nearby or distant monitors;

An internal device sufficiently small to also lay contained within the dermal lymphatic sinus;

An internal device surgically embedded in soft tissues beneath the dermis, i.e., in the subcutis.

The device to which the sensor communicates can receive signals through direct physical connections or wireless digital signaling, such as, but not limited to, Bluetooth.

The sensor can measure glucose or other analytes, such as ions, proteins and glycoproteins, lipids, other sugars, ingested nutrients or drugs/toxins or their metabolites.

The sensor can be coated with biologic or synthetic molecules (including, but not limited to chitosan, hyaluronic acid, Teflon®, glycosaminoglycans such as Heparin, Heparin sulfate, chondroitin sulfate etc. that are antifibrotic and/or anti-inflammatory around the sensor leading to consistent signaling over time greater than is achieved through current, imprecisely placed sensors.

Uses for the device would include continuous monitoring of blood sugar in patients with type 1 or type 2 diabetes mellitus, electrolyte imbalances in individuals in exposed environmental conditions such as soldiers and extreme sports participants, uric acid levels in patients with gout, etc.

According to the American Diabetes Association in 2012, 29.1 million Americans, or 9.3% of the population, had diabetes.

Approximately 1.25 million American children and adults have type 1 diabetes.

Undiagnosed: Of the 29.1 million, 21.0 million were diagnosed, and 8.1 million were undiagnosed.

Prevalence in Seniors: The percentage of Americans age 65 and older remains high, at 25.9%, or 11.8 million seniors (diagnosed and undiagnosed).

New Cases: 1.4 million Americans are diagnosed with diabetes every year.

Prediabetes: In 2012, 86 million Americans age 20 and older had prediabetes; this is up from 79 million in 2010.

Deaths: Diabetes remains the 7th leading cause of death in the United States in 2010, with 69,071 death certificates listing it as the underlying cause of death, and a total of 234,051 death certificates listing diabetes as an underlying or contributing cause of death.

Diabetes in Youth

About 208,000 Americans under age 20 are estimated to have diagnosed diabetes, approximately 0.25% of that population.

Diabetes may be underreported as a cause of death. Studies have found that only about 35% to 40% of people with diabetes who died had diabetes listed anywhere on the death certificate and about 10% to 15% had it listed as the underlying cause of death.

The key to good health for a diabetic is to monitor their blood glucose levels regularly to be able to maintain a healthy lifestyle. Blood sticks have long been the method for daily monitoring but they are painful and burdensome which leads to a lack of compliance among those who are at risk.

A finger-prick blood glucose check gives you only one number in time. It's hard to know: Is your blood glucose rising, falling, or staying steady? A continuous glucose monitor (CGM), however, records hundreds of readings a day.

A CGM consists of three parts: a small under-the-skin sensor that measures glucose levels in what is known as interstitial fluid; a transmitter that attaches to the sensor and transfers data; and a receiver that displays glucose information and stores data. The sensor measures glucose every five minutes or so.

According to Diabetes Self-Management; although studies find that the sensor readings usually are close to fingerstick numbers, there can be significant differences (up to 15%). It takes glucose around 5-10 minutes to move from blood into tissue fluid, or back, so the CGM measures lag behind what's really happening in your blood if things are changing rapidly.

The CGM doesn't replace fingersticks. You still have to check your blood glucose level 2 to 4 times a day to keep the CGM calibrated. Calibration is an ongoing job with CGMS. They also say you should not make "treatment decisions" (like taking extra insulin) based on a CGMS reading without taking a conventional blood glucose reading first.

Acceptance of CGM in the diabetic community has been slow because of a number of reasons. They are not reliable due to variabilities in placement of the sensor, the fat level of the individual and the high costs which are not always covered by insurance.

The present invention provides for multiple means for a variety of health monitoring that are a reliable means of placement of CGM and similar type interstitial sensors and the use of a digital device that can alternatively read a test strip in a more rapid low cost means of monitoring glucose among other constituents.

All references cited herein are incorporated herein by reference in their entireties.

BRIEF SUMMARY OF THE INVENTION

The invention provides a device for guiding the implanting of a sensor within the skin of a subject, the device comprising: a housing that is adapted for placement on the outer skin of the subject and comprising: at least one insertion port contiguous with an insertion channel that is formed at a predetermined angle within said housing, said channel having an opening that is adapted to rest against the skin; an ultraviolet illuminator for illumination of a fluorescent material that is previously positioned within the reticular dermis of the subject that is located underneath said housing; a camera comprising a focus adjustment, said camera capturing an image of the skin, including the reticular dermis, located beneath said housing; and a display that permits a user to view said image when passing an applicator and/or sensor through said channel such that a tip of said applicator and/or sensor is positioned within the reticular dermis for delivering the applicator and/or sensor therein. The invention provides a device wherein said camera comprises a wireless transponder and said display is located remotely of said housing, said transponder providing said image to said remotely located display. The invention provides a device wherein said camera is adapted to couple to a smartphone for displaying said image thereon. The invention provides a device wherein the camera is a confocal microscope. The invention provides a device wherein the focal plane of the camera is adjusted via the display.

The invention provides a device wherein the display is a smartphone. The invention provides a device wherein said predetermined angle is a shallow angle.

The invention provides a method of delivering a sensor to the skin of a subject, the method comprising: administering an imaging agent to a subject, wherein the imaging agent collects in the target area of the subject's skin, wherein the target area is the reticular dermis of the skin of the subject, further wherein the imaging agent is a fluorescent agent; providing a device for guiding the implanting of an applicator and/or sensor within the skin of the subject, the device comprising: a housing comprising: at least one insertion port contiguous with an insertion channel that is formed at a predetermined angle within said housing, said channel having an opening that is adapted to rest against the skin; an ultraviolet illuminator for illumination a fluorescent material that is previously positioned within the reticular dermis of the subject that is located underneath said housing; a camera comprising a focus adjustment, said camera capturing an image of the skin, including the reticular dermis, located beneath said housing; and a display, associated with said housing, that permits a user to view said image when passing an applicator and/or sensor through said channel such that a tip of said applicator and/or sensor is positioned within the reticular dermis for delivering the sampler therein; applying the imaging device to the skin of the subject; illuminating the skin with the illuminator, thereby causing the imaging agent to fluoresce; using the display to adjust the focus of the confocal microscope into the plane of the fluorescence; inserting an applicator and/or sensor through the at least one insertion port into the sample area of the subject, wherein the user uses a display to follow the insertion of the applicator and/or sensor, wherein when the tip of the applicator and/or sensor is in the plane of the focus, the applicator and/or sensor is in the target area.

The invention provides a method wherein the method further comprises: providing a sensor device; inserting the sensor device through the applicator and/or sensor, wherein the applicator and/or sensor is a hollow cannula, into the target area, thereby delivering the sensor to the target area of the skin of the subject. The invention provides a method wherein the imaging is obtained in real time. The invention provides a method wherein the imaging is obtained episodically. The invention provides a device wherein the imaging agent is fluorescent. The invention provides a method wherein the imaging agent is selected from the group consisting of radiopaque materials, MRI imaging agents, ultrasound imaging agents, and optical imaging agents, so that the agent is suitable for the imaging method. The invention provides a method, wherein the sensor device is attached to the skin of the subject at an area selected from the group consisting of the upper arm, abdomen, waist, torso, and back of the subject. The invention provides a method wherein the sensor device is configured to provide data to an external device for registering and transmission of data from the sensor to monitors. The invention provides a method wherein the sensor device further comprises an internal device sufficiently small to also lay contained within the target area. The invention provides a method wherein the sensor device is configured to communicate data through direct physical connection to a processing device.

The invention provides a method wherein the sensor device is configured to communicate data through a wireless signal. The invention provides a method wherein the sensor device is configured to communicate data through a wireless digital signal. The invention provides a method wherein the wireless signal is Bluetooth®. The invention provides a method wherein the sensor device can measure analytes in the interstitial fluid of the dermal interstitial space. The invention provides a method wherein the sensor device can measure an analyte selected from the group consisting of glucose, ions, proteins, glycoproteins, lipids, sugars, ingested nutrients, or drugs, toxins, metabolites of drugs, metabolites of toxins, and combinations thereof. The invention provides a method wherein the sensor device is coated with biologic or synthetic molecule selected from the group consisting of chitosan, hyaluronic acid, Teflon®, glycosaminoglycans, Heparin, Heparin sulfate, chondroitin sulfate. The invention provides a method wherein the coating is antifibrotic and/or anti-inflammatory around the sensor leading to consistent signaling over time greater than is achieved through current, imprecisely placed sensors. The invention provides a method wherein the sensor device is configured for continuous monitoring of blood sugar in patients with type 1 or type 2 diabetes mellitus. The invention provides a method wherein the sensor device is configured for monitoring of electrolyte imbalances in a subject. The invention provides a method wherein the subject is selected from the group consisting of individuals in exposed environmental conditions, soldiers. and extreme sports participants. The invention provides a method wherein the sensor device is configured for monitoring of uric acid levels in patients with gout. The invention provides a method wherein the subject is selected from the group consisting of individuals exposed to chemical weapons, such as soldiers in war zones, first responders in terrorist attacks.

The invention provides a method of delivering a sensor to the skin of a subject, the method comprising: providing a trocar device comprising: a hollow cannula and an obturator component; inserting the trocar device at a shallow angle into a target area, wherein the target area is selected from the group consisting of the reticular dermis of the skin of the subject, further wherein lymph draining from the cannula confirms correct placement of the trocar; removing the obturator component leaving the hollow cannula; providing a sensor device; inserting the sensor device through the hollow cannula into the target area; thereby delivering the sensor to the target area of the skin of the subject. The invention provides a method wherein the sensor device is attached to the skin of the subject at an area selected from the group consisting of the upper arm, abdomen, waist, torso, and back of the subject. The invention provides a method wherein the sensor device is configured to provide data to an external device for registering and transmission of data from the sensor to monitors. The invention provides a method wherein the sensor device further comprises an internal device sufficiently small to also lay contained within the target area. The invention provides a method wherein the sensor device is configured to communicate data through direct physical connection to a processing device. The invention provides a method wherein the sensor device is configured to communicate data through a wireless signal. The invention provides a method wherein the sensor device is configured to communicate data through a wireless digital signal. The invention provides a method wherein the wireless signal is Bluetooth®. The invention provides a method wherein the sensor device can measure analytes in the interstitial fluid of the dermal interstitial space. The invention provides a method wherein the sensor device can measure an analyte selected from the group consisting of glucose, ions, proteins, glycoproteins, lipids, sugars, ingested nutrients, or drugs, toxins, metabolites of drugs, metabolites of toxins, and combinations thereof. The invention provides a method wherein the sensor device is coated with biologic or synthetic molecule selected from the group consisting of chitosan, hyaluronic acid, Teflon®, glycosaminoglycans, Heparin, Heparin sulfate, chondroitin sulfate. The invention provides a method wherein the coating is antifibrotic and/or anti-inflammatory around the sensor leading to consistent signaling over time greater than is achieved through current, imprecisely placed sensors. The invention provides a method wherein the sensor device is configured for continuous monitoring of blood sugar in patients with type 1 or type 2 diabetes mellitus. The invention provides a method wherein the sensor device is configured for monitoring of electrolyte imbalances in a subject. The invention provides a method wherein the subject is selected from the group consisting of individuals in exposed environmental conditions, soldiers. and extreme sports participants. The invention provides a method wherein the sensor device is configured for monitoring of uric acid levels in patients with gout. The invention provides a method wherein the subject is selected from the group consisting of individuals in exposed to chemical weapons, such as soldiers in war zones, first responders in terrorist attacks.

The invention provides a device for collecting a sample from the skin of a subject, the device comprising: at least one trocar device comprising: a hollow cannula and an obturator component, the trocar device having a tip, a length, and a tip sharpness; and a trocar actuator coupled to the trocar configured to drive the trocar into the skin of the subject upon activation; wherein the tip sharpness and the actuator allow the trocar to pass through an outer layer of the skin upon activation, and the length is limited such that the tip does not extend past a desired depth below the surface of the skin of the subject, wherein the desired depth is located in the reticular dermis of the subject. The invention provides a device wherein the outer layer of the skin is the epidermis and the desired depth is located in the upper half of the reticular dermis. The invention provides a device wherein the at least one sample is collected from the subject following activation via the trocar. The invention provides a device wherein the at least one sample collected from the subject is lymph. The invention provides a device wherein the trocar is a hollow trocar, and further wherein the sample is lymph and is collected following activation via the hollow trocar. The invention provides a device wherein the device is configured to deliver the trocar to the skin of the upper arm of the subject and wherein the desired depth is 100 micrometers to 2 millimeters below the outer surface of the skin. The invention provides a device wherein the device is configured to deliver the trocar to the skin of the abdomen of the subject and wherein the desired depth is 100 micrometers to 1.9 millimeters below the outer surface of the skin. The invention provides a device further comprising an engagement element configured to adhere to the skin of the subject such that the engagement element resists deformation of the skin surface caused by the trocar during activation. The invention provides a device wherein the engagement element comprises an adhesive material and wherein the adhesive material is configured to form a nonpermanent bond to the skin of the subject, the bond being of sufficient strength to resist the deformation of the skin surface caused by the trocar during activation. The invention provides a device further comprising a tensile membrane having an upper surface and a lower surface, wherein the adhesive material is coupled to the lower surface of the tensile membrane. The invention provides a device wherein the adhesive material includes a first hole and the tensile membrane includes a second hole aligned with the first hole, wherein the first and second holes define a channel, the channel having a first end and a second end, the channel in axial alignment with the trocar, wherein at least the tip extends past the second end of the channel following activation.

The invention provides a device for collecting a sample from the skin of a subject, the device comprising: at least one trocar device comprising: a hollow cannula and an obturator component, the trocar device having a tip, a length, and a tip sharpness the hollow trocar coupled to a conduit, wherein the conduit provides fluid communication between the sample and the hollow trocar, such that the sample is permitted to flow from the hollow cannula sample to the sample collector; and a trocar actuator coupled to the trocar configured to drive the trocar into the skin of the subject upon activation; and an engagement element configured to adhere to the skin of the subject such that the engagement element resists deformation of the skin surface caused by the hollow trocar during activation; wherein at least one of the tip sharpness, the actuator and the engagement element is configured to reduce deformation of the skin surface of the subject caused by the hollow trocar following activation, and further wherein the trocar length allows the tip of the hollow trocar to be delivered to the reticular dermis of the subject. The invention provides a device wherein the at least one sample collected from the subject is lymph. The invention provides a device wherein the liquid sample is delivered to the collector device following activation. The invention provides a device wherein the engagement element comprises an adhesive material, wherein the adhesive material is configured to form a nonpermanent bond to the skin of the subject, the bond being of sufficient strength to resist the deformation of the skin surface caused by the hollow trocar during activation.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF PREFERRED EMBODIMENTS OF THE INVENTION

As used herein, the term "dermal interstitial sinus" refers to the middle to lower region of the dermis, i.e., the reticular dermis which communicates directly with the systemic lymphatic circulation and, from there, into the vascular system.

As used herein, "intradermal" refers to administration of a biologically active agent into the dermis in such a manner that the agent readily reaches the dermal interstitial sinus. Such can result from placement of the agent in the middle to lower region of the dermis, i.e., the reticular dermis. In certain embodiments, the invention provides for the controlled delivery of a biologically active agent in this dermal compartment below the papillary dermis in the newly discovered interstitial sinus of the reticular dermis which communicates directly with the systemic lymphatic circulation and, from there, into the vascular system. In certain embodiments, the invention provides for sampling of the fluid in the interstitial sinus of the reticular dermis which communicates directly with the systemic lymphatic circulation and, from there, into the vascular system, and can therefore serve as as a medium to test for biological, chemical, and/or pharmacological markers from the subject.

The term "administration" of the pharmaceutically active compounds and the pharmaceutical compositions defined herein. "Ameliorate" or "amelioration" means a lessening of the detrimental effect or severity of the disease in the subject receiving therapy, the severity of the response being determined by means that are well known in the art.

By "compatible" herein is meant that the components of the compositions which comprise the present invention are capable of being commingled without interacting in a manner which would substantially decrease the efficacy of the pharmaceutically active compound under ordinary use conditions.

By "pharmaceutically acceptable" or "pharmacologically acceptable" is meant a material which is not biologically or otherwise undesirable, i.e., the material may be administered to an individual without causing undesirable biological effects or interacting in a deleterious manner with any of the components of the composition in which it is contained.

As used herein, a "pharmaceutically acceptable carrier" is a material that is relatively nontoxic and generally inert and does not affect the functionality of the active ingredients adversely. Examples of pharmaceutically acceptable carriers are well known and they are sometimes referred to as diluents, vehicles or excipients. The carriers may be organic or inorganic in nature. In addition, the formulation may contain additives such as flavoring agents, coloring agents, thickening or gelling agents, emulsifiers, wetting agents, buffers, stabilizers, and preservatives such as antioxidants.

The term "pharmaceutical composition" as used herein means a composition that is made under conditions such that it is suitable for administration to, for example, humans, e.g., it is made under GMP conditions and contains pharmaceutically acceptable excipients, e.g., without limitation, stabilizers, pH adjusting agents, bulking agents, buffers, carriers, diluents, vehicles, solubilizers, and binders.

As used herein, the term "subject" encompasses mammals and non-mammals. Examples of mammals include, but are not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or sex.

As used herein, the terms "treating" or "treatment" of a disease include preventing the disease, i.e. preventing clinical symptoms of the disease in a subject that may be exposed to, or predisposed to, the disease, but does not yet experience or display symptoms of the disease; inhibiting the disease, i.e., arresting the development of the disease or its clinical symptoms, such as by suppressing or relieving the disease, i.e., causing regression of the disease or its clinical symptoms.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, "targeted sampling" means the use of intradermal sampling from particular specific tissues and/or organs and/or a biological entity not otherwise accessed or understood to be accessed by the conventional sampling methods.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-beta hydroxycholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free bet-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, beta; lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi*/rangeli, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin®, Cylert™, Preludin™, Didrex®, PreState™, Voranil™, Sandrex™ Plegine™); depressants (barbituates, methaqualone, tranquilizers such as Valium®, Librium™ Miltown®, Serax™, Equanil®, Tranxene®); hallucinogens (phencyclidine, lysergic acid, mescaline, peyote, psilocybin); narcotics (heroin, codeine, morphine, opium, meperidine, Percocet®, Percodan®, Tussionex®, Fentanyl®, Darvon®, Talwin®, Lomotil®); designer drugs (analogs of fentanyl, meperidine, amphetamines, methamphetamines, and phencyclidine, for example, Ecstasy™); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The terms "sensor" and "sensor system" as used herein are broad terms, and are to be given their ordinary and customary meaning to a person of ordinary skill in the art (and are not to be limited to a special or customized meaning), and refer without limitation to a device, component, or region of a device by which an analyte can be quantified.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte. The sensing region generally comprises a non-conductive body, a working electrode (anode), and can include a reference electrode (optional), and/or a counter electrode (cathode) forming electrochemically reactive surfaces on the body.

The terms "continuous" and "continuously" as used herein are broad terms, and are to be given their ordinary and customary meanings to a person of ordinary skill in the art (and are not to be limited to a special or customized meaning), and refer without limitation to the condition of being marked by substantially uninterrupted extension in space, time or sequence. In one embodiment, an analyte concentration is measured continuously or continually, for example at time intervals ranging from fractions of a second up to, for example, 1, 2, or 5 minutes, or longer. It should be understood that continuous glucose sensors generally continually measure glucose concentration without required user initiation and/or interaction for each measurement. These terms include situations wherein data gaps can exist (e.g., when a continuous glucose sensor is temporarily not providing data).

Skin

The skin comprises two layers, the outer or upper surface called the epidermis, and the internal surface referred to as the dermis. The epidermis does not contain any blood vessels and it is dependent on the underlying dermis for nutrient delivery and waste disposal via diffusion. The inner layer, the dermis, is composed of two layers, the more superficial papillary dermis and the deeper reticular dermis. The papillary dermis is thinner and consists primarily of loose connective tissue containing small capillaries, elastic fibers, reticular fibers and some collagen. The deeper reticular dermis consists of a thicker connective tissue containing larger blood vessels, interlaced elastic fibers and core spindles of collagen fibers arranged in layers parallel to the surface. The reticular layer also contains many antigen-presenting cells, fibroblasts, mast cells, nerve endings, and lymphatics. Because of the high amount of blood vessels, lymphatics, and antigen presenting cells in the dermis, this is an ideal site as a medium to test for biological, chemical, and/or pharmacological markers from the subject.

Intradermal Sampling

As used herein, sampling from the intradermal compartment is intended to mean sampling of the dermis in such a manner that the sample is a fluid from the richly vascularized reticular dermis and and/or lymphatic vessels. Such can result from placement of the applicator and/or sensor and/or cannula in the reticular region of the dermis, i.e., the upper portion of the reticular dermis. In exemplary embodiments, the applicator is a cannula. The controlled sampling in this dermal compartment below the papillary dermis in the reticular dermis, but sufficiently above the interface between the dermis and the subcutaneous tissue, should enable an efficient (outward) migration of the lymphatic fluid from the lymphatic microcapillary bed (in the papillary dermis), where it can be sampled. In some embodiments, placement of a trocar predominately at a depth of at least about 0.3 mm, more preferably, at least about 0.4 mm and most preferably at least about 0.5 mm up to a depth of no more than about 2.5 mm, more preferably, no more than about 2.0 mm and most preferably no more than about 1.7 mm will result in efficient sampling of the lymphatic fluid.

In accordance with the invention microneedle-based systems or any other means known to one skilled in the art to sample the intradermal compartment. Micro-cannula- and microneedle-based methodology and devices may also be used. Standard steel cannula can also be used for intradermal sampling. These methods and devices include the sampling through narrow gauge (30 G or narrower) "microcannula" with a limited depth of penetration (typically ranging from 10 microm to 2 mm), as defined by the total length of the cannula or the total length of the cannula that is exposed beyond a depth-limiting hub feature.

The intradermal sampling in accordance with the present invention are particularly beneficial in the diagnosis of the diseases including chronic and acute diseases which include, but are not limited to, lymphoma, melanoma, leukemia, breast cancer, colorectal cancer, cancer metastasis, diseases of the lymphatic system, any disease affecting the lymphnodes, e.g., axillary, politeal, lingual, viral diseases, e.g., HIV, immune disorders such as rejection, metabolic disorders, diabetes, and infectious diseases. The present invention is useful for diagnostic procedures including, but not limited to, surgical methods, biopsies, non-invasive screening and image-guided biopsies.

Imaging Agents

The present invention encompasses delivering imaging agents suitable for imaging by one or more imaging techniques, for example to identify the target area of the skin. Any imaging agent known in the art is contemplated within the methods and compositions of the invention. In some embodiments, the contrast agents are in particulate form and are adapted to be preferentially taken up by the lymphatic system upon administration. These contrast agents can be radiopaque materials, MRI imaging agents, ultrasound imaging agents, and any other contrast agent suitable for a device that images an animal body. Contrast agents for use in the methods of the invention are preferably nontoxic and/or non-radioactive. There are two major classes of contrast agents: paramagnetic and superparamagnetic; each of which is contemplated within the methods of the invention. Paramagnetic agents have unpaired electron spins that facilitate relaxation of nuclei, usually water protons, that can closely approach them (within 1 nm). These agents decrease both T1 and T2, are effective in uM concentrations, and can be incorporated in chelates with favorable biodistribution and toxicity profiles. Schering's patented product, GdDTPA (gadolinium diethylenetriaminepentaacetic acid), is an outstanding example of several commercially available such agents. In some embodiments the contrast agents are incorporated into macromolecules to avoid uptake by the systemic circulation. Combination with albumin, other biological molecules of appropriate size, latex, dextran, polystyrene or other nontoxic natural or synthetic polymer, or encapsulation in liposomes, can be accomplished using methods known to those skilled in the art.

The invention further encompasses non-specific contrast agents including but not limited to: MRI contrast agents (e.g., gadolinium, paramagnetic particles, super-paramagnetic particles), ultrasound contrast agents (e.g., microbubbles), CT contrast agents (e.g., radiolabels), X-Ray contrast agents (e.g., Iodine), PET contrast agents (e.g., any 2 photon emitter, F19, Fluoro-deoxy-glucose), Photoacoustic contrast agents (e.g., dyes, various light absorbing molecules), Optical contrast agents (e.g., Fluorescent: CY5, squaraines, near infrared dyes, i.e. indocyanine green, lanthanide fluors (e.g., Europium, Turbium).

In a particular example, microbubble ultrasound contrast agent is delivered as described herein. An ultrasound probe is positioned either at the injection site or at a regional lymph node site. Although not intending to be bound by a particular mechanism of action the contrast agent is delivered to the intradermal compartments and immediately travels through the lymphatic vessels and to the lymph node. The ultrasound probe detects the contrast agent as it passes beneath the probe. Both diagnostic flow rate and architecture information, including obstructions, can be obtained. In this embodiment, the images can be obtained continuously (real time) or in an episodic manner.

In some embodiments, magnetic resonance images further comprise an additional step of making sure to pre-image the subject prior to injection of the agent, e.g., contrast agent. In some embodiments, Multiple images post injection are obtained over time and compared to the pre-image. The invention encompasses methods for detection and location of lymph nodes, as well as information concerning other tissues, organs and biological entities using methods disclosed herein and known to those skilled in the art, e.g., CT, PET, SPECT, Optical (e.g., Fluorescent, Chemiluminescent), Confocal, and X-Ray imaging.

Presence of the imaging agent can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), single photon emission computer tomography (SPECT), X-Ray, Optical (spectrophotometric) imaging, confocal imaging, and sonography.

Confocal Laser Scanning Microscopy

One of the preferred embodiments of detecting the target area of the skin relies on the use of confocal laser scanning microscopy, which in a further preferred embodiment may use UV light sources. Confocal microscopy offers several advantages over conventional optical microscopy, one of the most important being the elimination of out-of-focus information that distorts the image, controllable depth of field and sub-micron resolution. A further advantage of confocal microscopy is that fluorescence of various portions of the specimen that are out-of-focus can be filtered out and so do not interfere with the portions or sections that are in-focus thereby yielding an image that is considerably sharper and shows a better resolution than a comparable image obtained by classical light microscopy.

The basic principle of confocal scanning microscopy is the use of a screen with a pinhole at the focal point of the microscope lens system which is "conjugate" to the point at which the objective lens is focussed. Only light coming from the focal point of the objective is focussed at the pinhole and can pass through to the detector, which e.g. may be a charge couple device (CCD). Light coming from an out-of-focus section of the sample will be nearly completely filtered out.

Thus, a confocal microscope has a significantly better resolution than a conventional microscope for the x- and y-direction. Furthermore, it has a smaller depth of field in the z-direction. By scanning the focal point through the sample, it is thus possible to view different planes of a sample and to then rebuild a 3-dimensional image of the sample. Furthermore, confocal microscopy is compatible with different wavelengths of light.

If a confocal laser-scanning microscope is integrated in e.g. an endoscopic device, an actuator may be used to scan the confocal microscope over the tissue of interest. A first coarse scan can then be used to determine the morphology of the tissue and the tissue in which an up-regulation of e.g. TERT is seen can be identified from this screen.

For confocal scanning microscope one may use monochromatic or polychromatic light however, monochromatic UV light with a wavelength between 240 nm and 280 nm may be preferred. As a confocal laser scanning microscope one may use a microscope such as LEICA® DMLM and having a Qimaging Retiga 2000R FASTCooled Mono 12-bit camera unit (www.qimaging.com) for measuring the signal intensity of the fluorescence signal. A Leica® DM6000 may be particularly preferred.

For the purposes of the present invention where the reticular dermis is to be targeted, the confocal laser-scanning microscope may be integrated or relied upon. Systems, which are known for this purpose, differ mostly in the manner in which the image is scanned. Two rather advanced commercial systems are available, e.g. from Optiscan and Mauna Kir Technology. The Mauna Kir instrument is a proximally scanned system where the image is transferred down the endoscope with a coherent fibre optic bundle. A selected point or fibre is imaged into the sampled tissue at the distal end. This confocal endomicroscope may be delivered through the working channel of an endoscope. Since the field of view of the endomicroscope is small, placement of the probe is guided by standard video endoscopy. Hence, the endoscope platform must include both a video imager and the confocal microscope. Of course, the endoscope unit may also comprise or be coupled to computer devices and software packages that allow processing of the obtained images.

Detection units may e.g. be Optronics DEI-700 CE three-chip CCD camera connected via a BQ6000 frame-grabber board to computer. Alternatively one may use a Hitachi HV-C20 three-chip CCD camera. Software packages for image analysis may e.g. be the Bioquant True Color Windows 98 v3.50.6 image analysis software package (R&M Biometrics, Nashville, Tenn.) or Image-Pro Plus 3.0 image analysis software. Another system that may be used is the BioView Duet system (BioView Ltd, Rehovot, Israel which is based on a dual mode, fully automated microscope (Axioplan 2, Carl Zeiss, Jena, Germany), an XY motorized 8-slides stage (Marzhauscr, Wetzler, Germany) a 3CCD progressive scan color camera (DXC9000, Sony, Tokyo, Japan) and a computer for control and analysis of the system and the data. Optiscan has developed an endomicroscope employing distal scanning.

Microscopy

Microscopy methods that may be used with this invention include but are not limited to bright field, oblique illumination, dark field, dispersion staining, phase contrast, differential interference contrast (DIC), polarized light, epifluorescence, interference reflection, fluorescence, confocal (including CLASS), confocal laser scanning microscopy (CLSM), structured illumination, stimulated emission depletion, electron, scanning probe, infrared, laser, widefield, light field microscopy, lensless on-chip holographic microscopy, digital and conventional holographic microscopy, extended depth-of-field microscopy, optical scatter imaging microscopy, deconvolution microscopy, defocusing microscopy, quantitative phase microscopy, diffraction phase microscopy, confocal Raman microscopy, scanning acoustic microscopy and X-ray microscopy. Magnification levels used by microscopy may include, as nonlimiting examples, up to 2×, 5×, 10×, 20×, 40×, 60×, 100×, 100×, 1000×, or higher magnifications. Feasible magnification levels will vary with the type of microscopy used.

Fluorescence Microscopy

Fluorescence microscopy generally involves labeling of cells or other samples with fluorescent labels, described in more detail below. Microscopic imaging of fluorescently labeled samples may gather information regarding the presence, amounts, and locations of the target that is labeled at a given moment in time or over a period of time. Fluorescence may also be used to enhance sensitivity for detecting cells, cellular structures, or cellular function. In fluorescence microscopy, a beam of light is used to excite the fluorescent molecules, which then emit light of a different wavelength for detection. Sources of light for exciting fluorophores are well known in the art, including but not limited to xenon lamps, lasers, LEDs, and photodiodes. Detectors include but are not limited to PMTs, CCDs, and cameras.

Fluorimetry refers to measuring the light emitted by a fluorescent molecule coupled to a subject upon exciting the fluorescent molecule with incident light. Fluorimetry may use any of the fluorescent molecules, labels, and targets. In some embodiments, fluorimetry uses substrate molecules that change in fluorescence based on an enzymatic activity, such as converting NAD+ to NADH or vice versa or producing beta-galactosidase from a precursor molecule. Fluorimetry may be used with a polarized excitation source to measure fluorescence polarization or anisotropy of a subject, which may provide information about the size and/or binding state.

Illuminator

An illuminator or light source may be any device capable of emitting energy along the electromagnetic spectrum. A light source may emit light along a visible spectrum. In one example, a light source may be a light-emitting diode (LED) (e.g., gallium arsenide (GaAs) LED, aluminum gallium arsenide (AlGaAs) LED, gallium arsenide phosphide (GaAsP) LED, aluminum gallium indium phosphide (AlGaInP) LED, gallium(III) phosphide (GaP) LED, indium gallium nitride (InGaN)/gallium(III) nitride (GaN) LED, or aluminum gallium phosphide (AlGaP) LED). In another example, a light source can be a laser, for example a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlAs/GaAs) laser. Other examples of light sources may include but are not limited to electron stimulated light sources (e.g., Cathodoluminescence, Electron Stimulated Luminescence (ESL light bulbs), Cathode ray tube (CRT monitor), Nixie tube), incandescent light sources (e.g., Carbon button lamp, Conventional incandescent light bulbs, Halogen lamps, Globar, Nernst lamp), electroluminescent (EL) light sources (e.g., Light-emitting diode—Organic light-emitting diodes, Polymer light-emitting diodes, Solid-state lighting, LED lamp, Electroluminescent sheets Electroluminescent wires), gas discharge light sources (e.g., Fluorescent lamps, Inductive lighting, Hollow cathode lamp, Neon and argon lamps, Plasma lamps, Xenon flash lamps), or high-intensity discharge light sources (e.g., Carbon arc lamps, Ceramic discharge metal halide lamps, Hydrargyrum medium-arc iodide lamps, Mercury-vapor lamps, Metal halide lamps, Sodium vapor lamps, Xenon arc lamps). Alternatively, a light source may be a bioluminescent, chemiluminescent, phosphorescent, or fluorescent light source.

The light source may be capable of emitting electromagnetic waves in any spectrum. For example, the light source may have a wavelength falling between 10 nm and 100 microm. The wavelength of light may fall between 100 nm to 5000 nm, 300 nm to 1000 nm, or 400 nm to 800 nm. The wavelength of light may be less than, and/or equal to 10 nm, 100 nm, 200 nm, 300 nm, 400 nm, 500 nm, 600 nm, 700 nm, 800 nm, 900 nm, 1000 nm, 1100 nm, 1200 nm, 1300 nm, 1500 nm, 1750 nm, 2000 nm, 2500 nm, 3000 nm, 4000 nm, or 5000 nm.

One or more of a plurality of light sources may be provided. In some embodiments, each of the plurality of light sources may be the same. Alternatively, one or more of the light sources may vary. The light characteristics of the light emitted by the light sources may be the same or may vary. The light sources may be independently controllable.

Camera

The device may be used with any standard compact digital imaging device (e.g., a charge-coupled device (CCD) or complementary metal-oxide-semiconductor (CMOS) sensors) as the image acquisition device. The example device shown in a) has an external electrical power source, the two LED arrays for illuminating the object/surface to be imaged, and a commercially available digital camera securely fixed to light-weight metal frame equipped with a convenient handle for imaging. A multi-band filter is held in front of the digital camera to allow wavelength filtering of the detected optical signal emanating from the object/surface being imaged. The camera's video/USB output cables allow transfer of imaging data to a computer for storage and subsequent analysis. This example uses a commercially-available 8.1-megapixel Sony digital camera (Sony Cybershot DSC-T200 Digital Camera, Sony Corporation, North America). This camera may be suitable because of i) its slim vertical design which may be easily integrated into the enclosure frame, ii) its large 3.5-inch widescreen touch-panel LCD for ease of control, iii) its Carl Zeiss 5× optical zoom lens, and iv) its use in low light (e.g., ISO 3200). The device may have a built-in flash which allows for standard white light imaging (e.g., high-definition still or video with sound recording output). Camera interface ports may support both wired (e.g., USB) or wireless (e.g., Bluetooth®, WiFi, and similar modalities) data transfer or $3^{rd}$ party add-on modules to a variety of external devices, such as: a head-mounted display, an external printer, a tablet computer, laptop computer, personal desk top computer, a wireless device to permit transfer of imaging data to a remote site/other device, a global positioning system (GPS) device, a device allowing the use of extra memory, and a microphone. The digital camera is powered by rechargeable batteries, or AC/DC powered supply. The digital imaging device may include, but is not limited to, digital cameras, webcams, digital SLR cameras, camcorders/video recorders, cellular telephones with embedded digital cameras, Smartphones™, personal digital assistants (PDAs), and laptop computers/tablet PCs, or personal desk-top computers, all of which contain/or are connected to a digital imaging detector/sensor.

This light signal produced by the excitation/illumination light sources may be detected by the imaging device using optical filter(s) (e.g., those available from Chroma Technology Corp, Rockingham, Vt., USA) that reject the excitation light but allow selected wavelengths of emitted light from the tissue to be detected, thus forming an image on the display. There may for example be an optical filter holder attached to the enclosure frame in the digital camera lens which may accommodate one or more optical filters with different discrete spectral bandwidths, such as the device with the LED arrays turned on to emit bright violet/blue light, with a single emission filter in place or the device may use a multiple-optical filter holder used to select the appropriate filter for desired wavelength-specific imaging.

The device may be modified by using optical or variably oriented polarization filters (e.g., linear or circular combined with the use of optical wave plates) attached in a reasonable manner to the excitation/illumination light sources and the imaging detector device. In this way, the device may be used to image the tissue surface with polarized light illumination and non-polarized light detection or vice versa, or polarized light illumination and polarized light detection, with either white light reflectance and/or fluorescence imaging. This may permit imaging with minimized specular reflections (e.g., glare from white light imaging), as well as enable imaging of fluorescence polarization and/or anisotropy-dependent changes in connective tissues (e.g., collagens and elastin) within the target area and surrounding normal tissues.

All components of the imaging device may be integrated into a single structure, such as an ergonomically designed enclosed structure with a handle, allowing it to be comfortably held with one or both hands. The device may also be provided without any handle. The device may be light weight, portable, and may enable real-time digital imaging (e.g., still and/or video) of any target surface (for example, the skin and/or oral cavity, which is also accessible) using white light, fluorescence and/or reflectance imaging modes. The device may be scanned across the body surface for imaging by holding it at variable distances from the surface, and may be used in a lit environment/room to image white light reflectance/fluorescence. The device may be used in a dim or dark environment/room to optimize the tissue fluorescence signals, and minimize background signals from room lights. The device may be used for direct (e.g., with the unaided eye) or indirect (e.g., via the viewing screen of the digital imaging device) visualization of the target area and surrounding tissues.

The device may also be embodied as not being hand-held or portable, for example as being attached to a mounting mechanism (e.g., a tripod or stand) for use as a relatively stationary optical imaging device for white light, fluorescence and reflectance imaging of objects, materials, and surfaces (e.g., a body). This may allow the device to be used on a desk or table or for 'assembly line' imaging of objects, materials and surfaces. In some embodiments, the mounting mechanism may be mobile.

Other features of this device may include the capability of digital image and video recording, possibly with audio, methods for documentation (e.g., with image storage and analysis software), and wired or wireless data transmission for remote telemedicine/E-health needs. For example, the device may be a a mobile communication device such as a cellular telephone. The telephone may be fitted into the holding frame for convenient imaging. The images from the camera, for example in a cellular telephone or a confocal camera, may be sent wirelessly to another cellular telephone, or wirelessly (e.g., via Bluetooth connectivity) to a personal electronic device or computer for image storage and analysis. This demonstrates the capability of the device to perform real-time hand-held fluorescence imaging and wireless transmission to a remote site/person as part of a telemedicine/E-health care infrastructure.

Analyte Sensor System

Figure 1:
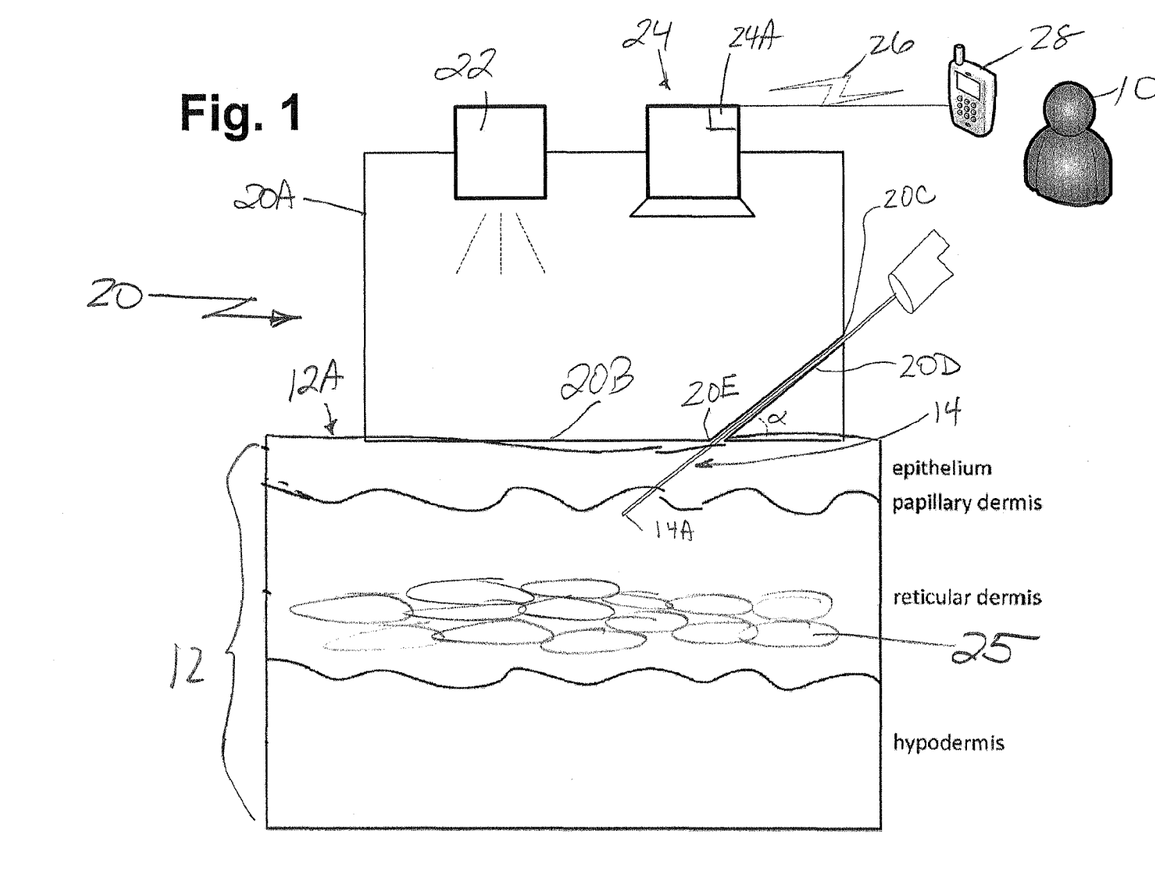
FIG. 1 depicts a diagrammatic view of a first embodiment of a device for guiding the implanting of a sensor within the skin of a subject and using a wireless connection to a user display.
Figure 2:
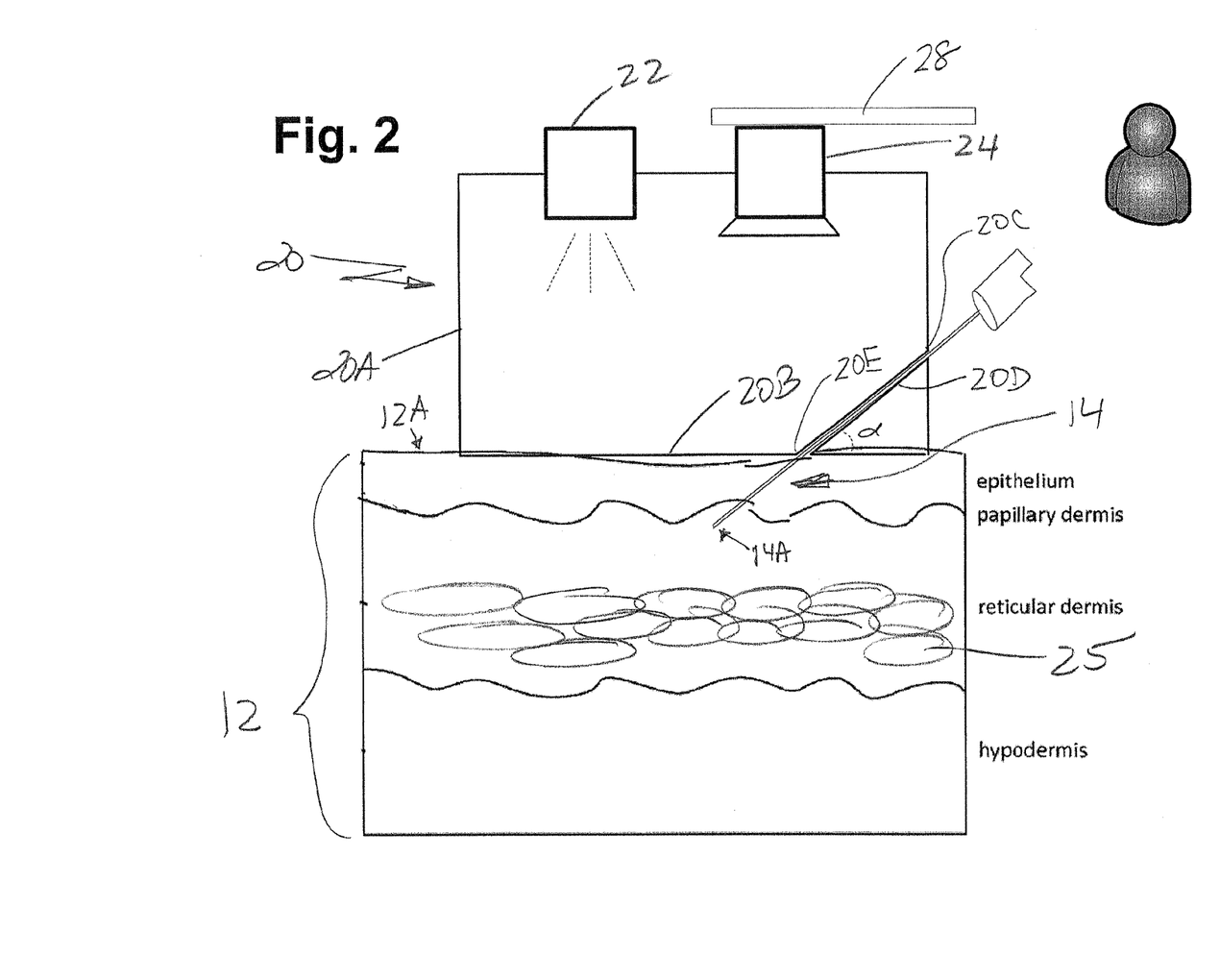
FIG. 2 depicts a diagrammatic view of a second embodiment of a device for guiding the implanting of a sensor within the skin of a subject which uses a direct coupling to the user display.

As shown in FIG. 1, the device 20 of the present invention comprises a housing 20A that is adapted to be placed against the skin 12A of the patient. An ultraviolet (UV) illuminator 22 is positioned on a top surface of the housing 20A to activate a fluorescent dye 25 that has been previously-injected within the patient and which ultimately is positioned within the reticular dermis of the patient's skin layers 12, in accordance with the preceding and following discussion. The housing 20A also comprises a camera (e.g., a confocal lens device, including focus adjustment) 24 that can image the skin that is beneath the bottom portion 20B of the housing 20A. In addition, the housing 20A comprises a cannula insertion port 20C and channel 20D that is formed within the housing 20A at a predetermined angle alpha, preferably a shallow angle. The distal end of the channel 20D comprises an exit port 20E that is in contact with the skin surface 12D. The confocal lens device 24 may also comprise a transponder 24A for effecting a wireless (e.g., (e.g., Bluetooth®, WiFi, IRdA2, ZigBee™, WiMAX®, LTE, etc.) communication 26 to a remote computer display 28 (e.g., a smartphone, imaging display, etc.) to permit a user 10 to see the illuminated fluorescent dye 25 within the reticular dermis; alternatively, as shown in FIG. 2, the confocal lens device 24 may be adaptable to be directly coupled to the computer display 28 without the need for any transponder 24A and wireless communication 26.

In operation, the fluorescent dye 25 is injected within the patient and whereby this dye 25 makes its way within the reticular dermis, in accordance with the preceding and following discussion. The user 10 then places the housing 20A on the skin of the patient and activates the UV illuminator 22 and confocal lens device 24. The UV illuminator 22 illuminates the skin layers 12 and the fluorescent dye 25 then fluoresces. The confocal lens device 24 then transmits an image (either via the wireless transponder 24A or via direct coupling) which then appears in the user's computer display 28. While monitoring the display 28, the user 10 then inserts the cannula (e.g., a needle, etc.) into the insertion port 20C and down into the channel 20D, through the skin 12A and immediately stops the insertion as soon as the needle tip 14A appears in the fluorescent dye 25, thereby confirming that the needle tip 14A is properly disposed in the reticular dermis. The appearance of lymph fluid and/or fluorescent dye 25 within the transparent needle 14 provides another indicator that the proper location of the needle tip 14 within the reticular dermis. At that point, a sensor (e.g., a glucose sensor), hereinafter referred to as a "sampler" can be delivered through the needle 14 and ideally positioned within the reticular dermis.

Thus, the present invention 20 provides a simple, reliable and repeatable means for gaining access and/or disposing an item precisely within the reticular dermis.

In an exemplary system for monitoring a physiological analyte, the sensor system obtains a series of measurements relating to analyte levels in a user. The sensor system can be worn, for example, in the abdomen region of a patient. A small sensor can be placed on or into the patient to obtain readings of analyte values using, for example, subcutaneous analyte, lymphatic fluid analyte, reticular dermis analyte, or blood analyte readings. The sensor can be placed into the patient using a needle that extends into the patient, deposits the sensor, and then retracts and can be discarded. An applicator or other similar device can contain the needle and be used for inserting the sensor. The continuous analyte sensor system can also be a transdermal device, an intravascular device, or a non-invasive device.

The Continuous analyte sensor system may include a number of components to obtain analyte measurements, store the data, calculate analyte levels, communicate with dedicated display and perform other tasks. For example, although not illustrated, continuous analyte sensor system may include nonvolatile memory for storing historical data regarding analyte values, a processor, a battery, and a wireless transmitter. The wireless transmitter may provide any type of wireless communications, including a Bluetooth connection, WiFi connection, RF connection, and others. The wireless communications may occur, in some embodiments, between paired, authenticated devices, and may use encryption and other cryptographic techniques to ensure that communications remain confidential.

While illustrated as a single unit, the wireless transmitter may be removable from the continuous analyte sensor system and reusable with multiple sensors as the sensors are replaced. Further, the continuous analyte sensor system can include other components to facilitate data communications. For example, the continuous analyte sensor system may include wired ports, such as a USB port, Ethernet port, and others, for communicating with other devices and providing data relating to analyte levels. The continuous analyte sensor system may include the processing circuitry, such as a processor, memory, and a battery, as part of the sensor electronics. The sensor electronics may be included in the continuous analyte sensor system or the transmitter.

The sensor portion of the continuous analyte sensor system may be removable and replaceable, allowing a patient to change to a new sensor periodically, such as every week. Similarly, the transmitter may detach and be removable from the continuous analyte sensor system, allowing replacement as needed, such as every six months.

A Continuous analyte sensor system may obtain samples at predetermined intervals, such as every few seconds, every thirty seconds, every minute, or on demand in response to a command from a user. In one embodiment, the wireless transmitter can be turned off to conserve battery life, and measurements taken over a period of time can be wirelessly transmitted to dedicated display in a batch transfer. For example, the continuous analyte sensor system can wake up the wireless transmitter every five minutes, transfer data relating to analyte measurements taken over the last five minutes, and transfer the data to the dedicated display. The wireless transmitter can then be turned off again to conserve battery life. While an example of transferring data every five minutes has been provided, it will be appreciated that longer or shorter time periods can be used, and the time period can be configured by a user via dedicated display.

The system may have a state determined by the continuous analyte sensor system and its transmitter. One exemplary system state includes not started, such as when a sensor has not yet been inserted into the subject or when the user has not yet activated the continuous analyte sensor system. Another example is a sensor warm-up period, which may last for a period of time, such as two hours, when the sensor is warming up and acclimating to insertion in the user's body. The sensor warm-up state may also include a calibration period. Other examples of system states include in calibration or out of calibration. A sensor and/or continuous analyte sensor system may be in calibration when it has been calibrated within a predetermined interval, such as within the last twelve hours, and out of calibration if a predetermined duration (e.g. twelve hours) has passed since the last calibration. Another exemplary system state is sensor stopped. The sensor stopped state may occur, for example, when a user seeks to replace the sensor portion of the analyte sensor system.

Implementations described herein can include a system for a subject, or in exemplary embodiments, one or more caretakers (e.g., a parent, spouse or healthcare practitioner) to remotely monitor health characteristics of one or more subjects. The health characteristics can include an analyte concentration of a subject, such as glucose, or a bodily function, such as heart rate, blood pressure, temperature and the like. In addition, other characteristics of a subject can be monitored to facilitate care of a subject, such as a location of the subject, state of a subject (e.g., exercising, sleeping, or working) and the like. The health characteristics and other characteristics can be gathered using a subject monitoring system that incorporates a computing device, such as a smart phone, and one or more sensors, such a continuous glucose sensor, heart-rate monitor, GPS device, etc. Additionally, a user can manually input information into the computing device, such as meal information, medication administration times and amounts, and the like. The information gathered by the subject monitoring system can then be transmitted to one or more remote monitors used by caretakers. The caretaker(s) can then receive information about the subject's health condition using a remote monitoring system. In some implementations, a monitoring system can transmit information directly to the one or more remote monitors and/or the subject monitoring system transmits information first to a remote server, which then transmits information to the subject monitor.

The analyte sensor system of the preferred embodiments can be designed with a variety of alternative configurations. In some embodiments, the sensor is connected to a fluid connection device. The fluid connection device in these embodiments can be any standard fluid connection device known in the art, such as a fluid coupler, or a fluid coupler custom manufactured to preferred specifications. On its first side, the fluid coupler is configured to couple to an existing catheter or cannula. The catheter (or cannula) is typically inserted into a vascular access device and/or into a hospital subject during a hospital stay. For example, the catheter can be inserted into an arterial line (e.g., for removing blood samples or for measuring blood pressure using a pressure transducer) or a venous line (e.g., for intravenous delivery of drugs and other fluids). In general practice, the catheter is inserted into the subject's blood vessel, for example, and maintained there for a period of time during the subject's hospital stay, such as part of the stay or during the entire stay (e.g., perioperatively). In one alternative embodiment, another vascular access device (e.g., other than a catheter) can be used to receive the sensor. In yet another alternative embodiment, the sensor system of the preferred embodiments can be inserted into a vascular access device (e.g., rather than the vascular system directly). Some examples of vascular access devices include but are not limited to, catheters, shunts, automated blood withdrawal devices and the like.

In some embodiments, the sensor is inserted directly into, for example, the subject's reticular dermis system without a trocar or other medical device. In one such exemplary embodiment, a sheath covering the sensor is relatively rigid and supports the sensor during insertion. After the sensor has been inserted into the subject's skin, the supportive sheath is removed, leaving the exposed sensor in the subject's skin, such as the reticular dermis. In an alternative example, the sensor is inserted into, for example, a cannula and the cannula is removed, to leave the sensor in the subject's reticular dermis.

Sensors

Although the description herein refers to some implementations that include a continuous analyte sensor comprising a glucose sensor, the continuous analyte sensor may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used instead or as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like. In some implementations, other health characteristics of a host are monitored in addition to or instead of analyte monitoring described herein, including, but not limited to heart rate, blood pressure levels, blood oxygen levels, body temperature, caloric intake, medicament delivery and the like.

In an aspect, the sensor can include one or more optical sensors. An optical sensor can be configured to measure the optical absorption, optical emission, fluorescence, or phosphorescence, luminescence of an analyte or an associated tag or binding element, other tissues of interest, or combinations thereof. Such optical properties can be inherent optical properties of the analyte, e.g. auto fluorescence, or can be optical properties of materials added or introduced into the body of the subject that interact with the analyte, other tissues of interest, or combinations thereof. Optical sensing of materials in blood, for example, is described in Mattley et al., "Blood characterization using UV/VIS spectroscopy" Proc. SPIE Advances in Fluorescence Sensing Technology II, Joseph R. Lakowicz; Ed. Vol. 2388, p. 462-470, 1995 and U.S. Pat. Nos. 5,589,932 and 7,027,134, each of which is incorporated herein by reference.

The devices may include one or more sensors configured to sense the blood glucose levels in the subject. The one or more sensors can include a glucose sensor that is either an integral part of the device, wherein the sensors is operably connected to the programmable microprocessor as described herein, or is in a separate device, for example a glucose sensing device in wireless communication with the programmable microprocessor in the device described herein. A number of different glucose monitors have been described using, for example, pin prick, transdermal, or implantable devices. See, e.g., U.S. Pat. Nos. 4,436,094; 4,953,552; 5,497,772; U.S. Patent Applications 2010/0049021; 2010/0081910; each of which is incorporated herein by reference. The one or more sensors can include one or more electrochemical- or photochemical-based sensors wherein a measurable chemical reaction occurs in response to the presence of one or more analyte. For example, many electrochemical sensors use enzymes as specifiers for the analyte. The enzymes cause a chemical reaction, such as a reduction reaction, and electrons released by the reaction are transferred to a mediator molecule, which itself is converted. The mediator then transfers the electrons to an electrode for electrochemical measurement or transfers the electrons to an indicator molecule for photochemical responses. Ferrocene derivatives and hexacyanoferrate are examples of one-electron mediators. Quinones are an example of two-electron mediators. A glucose sensor included in the device uses as the specifier an oxidoreductase that oxidizes glucose to gluconolactone. Electrons from the glucose are then transferred to the oxidized form of a mediator molecule, which in turn delivers the electrons to an electrode. The amount of electric current generated is proportional to the amount of glucose in the sample, and electronics within the sensor convert the signal, and the signal is communicated to the programmable microprocessor or the electronics module that is operably connected to the programmable microprocessor. See, e.g., Hones, et al., Diabetes Techn & Therap, 10: Supplement 1 S10-S26, 2008. Examples of commercially available glucose monitors using such technology in measuring blood glucose levels of a subject include, but are not limited to, OneTouch® blood glucose monitors (LifeScan-Johnson & Johnson, Milpitas, Calif.), Accu-Chek® blood glucose monitors (F. Hoffman-Roche A G, Basel, Switzerland), and Ascencia® blood glucose monitors (Bayer HealthCare LLC, Tarrytown, N.Y.). In an aspect, the glucose sensor for measuring blood glucose levels of a subject can include a continuous monitoring system, examples of which include, but are not limited to Freestyle. Navigator® glucose monitor (Abbot Diabetes Care, Alameda, Calif.), Guardian® Real-Time glucose monitor (Medtronic MiniMed, Northridge, Calif.), and DexCom® SEVEN® glucose monitor (DexCom, San Diego, Calif.). See, e.g., Hermanides & DeVries, Diabetologia, 53: 593-596, 2010, which is incorporated herein by reference. The FreeStyle Navigator® glucose monitor, for example, is biocompatible chip implanted into the abdomen or back of the upper arm of a subject and includes an external receiver. Similarly, blood glucose sensor-enabled radio frequency identification (RFID) devices have been described for active monitoring of glucose. See, e.g., Moore, J. Diabetes Sci. Technol. 3: 180-183, 2009, which is incorporated herein by reference. Miniaturized (0.5 times 0.5 times 5 mm) implantable glucose sensors can include the GLUCOWIZZARD® implantable glucose sensor that senses glucose levels and transmits the information to a proximal communicator. See, e.g., BIORASIS Storrs/Mansfield, Conn. A bio-sensor chip can include a passive transponder, glucose sensor, and integrated circuitry. See, e.g., U.S. Pat. No. 7,125,382 to Zhou entitled "Embedded Bio-sensor System," which is incorporated herein by reference. See, e.g., Digital Angel Corporation, St. Paul, Minn. Other methods for continuous monitoring of blood glucose levels of a subject include transcutaneous fluorescence lifetime-based microsensors or subcutaneous microelectromechanical systems (MEMS)-based sensors. See, e.g., U.S. Pat. No. 6,304,766; Nielsen, et al., J. Diabetes Sci. Technol. 3: 98-109; Li, et al., J. Diabetes Sci. Technol. 2: 1066-1074, 2008, each of which is incorporated herein by reference.

The one or more sensors can be configured to include an assembly for in vivo microdialysis. In vivo microdialysis allows for continuous sampling from the interstitial fluid of a tissue with minimal influence on surrounding tissues and/or whole body function. A microdialysis probe can be inserted into a tissue of interest, and perfused at a constant flow rate with a physiological buffer, e.g., saline. The tip of the probe consists of a semi-permeable membrane through which compounds in the interstitial fluid of the tissue can diffuse and subsequently be sampled from the outlet tubing of the probe.

In an aspect, the one or more analytes can include, but are not limited to, utilizable glucose, produced and/or released glycerol, free fatty acids, cAMP (indicative of beta-adrenergic receptor stimulation), hexokinase and phosphofructokinase or their enzymatic activities or products.

The device can include one or more sensors configured to sense one or more other physiological conditions of the subject including, but not limited to, pH, pCO2, blood flow, blood pressure, skin temperature, core temperature, tissue temperature, or blood oxygenation. The one or more sensors can also be configured to sense measures of physical activity of the subject as a means for estimating daily energy expenditure. Measures of physical activity of a subject include, but are not limited to, body temperature, heart rate, skin resistance, motion/acceleration, and velocity.

The one or more sensors can include one or more temperature sensors configured to measure temperature in one or more tissues. The temperature sensor can be a thermistor, a thermocouple, or a resistive temperature detector.

The one or more sensors can include one or more sensors that are calorimeters configured to measure caloric intake and/or energy expenditure. In an aspect, the one or more calorimeter can include an indirect calorimeter configured to assess the physical activity of the subject by periodically monitoring heart rate, body temperature, skin resistance, motion/acceleration sensing, velocity and providing an estimate of caloric intake/energy expenditure. The indirect calorimeter can include one or more of a temperature sensor, a heart rate sensor, an accelerometer, a global positioning system, or a combination thereof. See, e.g., U.S. Patent Application 2009/0240113, which is incorporated herein by reference. An example of a wireless patch system configured for estimating energy expenditure has been described and includes sensors, electrodes, and accelerometers. This system measures a variety of physiological conditions including temperature, heart rate, respiratory rate, and skin conductivity and uses this information in an algorithm to calculate the number of calories consumed, the number of calories burned, and the net yield. See, e.g., U.S. Patent Application 2010/0049004, which is incorporated herein by reference. Other examples of calorie counters based on activity measurements have been described. See, e.g., U.S. Pat. Nos. 4,100,401; 4,159,416; 5,815,954; and 7,334,472, each of which is incorporated herein by reference. Other means for performing calorimetry include, but are not limited to, the Haldane gravimetric method, open-circuit calorimeter with mask, spirographic method, assessment of heat loss and oxygen consumption.

The one or more sensors can be configured to detect an analyte that includes, but is not limited to, a biological marker, an antibody, an antigen, a peptide, a polypeptide, a neuropeptide, a protein, a complex, an enzyme, a hormone, a neurotransmitter, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a saccharide, a polysaccharide, a glycoprotein, a metal, an electrolyte, a metabolite, an organic compound, an organophosphate, a drug, a therapeutic, a gas, a pollutant, or a tag. The one or more sensors can include one or more binding elements configured to interact with an analyte including, but not limited to, binding molecules, recognition elements, antibodies or fragments thereof, oligonucleotide or peptide based aptamers (see, e.g., Mok & Li Sensors 8: 7050-7084, 2008, which is incorporated herein by reference), receptors or ligands, artificial binding substrates (e.g. those formed by molecular imprinting), or any other examples of molecules and/or substrates capable of interacting with an analyte.

The one or more sensors can include a single sensor or an array of sensors, and is not limited to a particular number or type of sensors. The one or more sensors can be very small, comprising a sensor or array of sensors, having, for example, a biosensor, a chemical sensor (Snow Science, 2005, 307: 1942-1945), a gas sensor (Hagleitner et al., Nature, 2001 414:293-296), an electronic nose, a nuclear magnetic resonance imager (Yusa et al., Nature, 2005, 343:1001-1005). The foregoing references are each incorporated herein by reference. Further examples of sensors are provided in The Biomedical Engineering Handbook, Second Edition, Volume I, J. D. Bronzino, Ed., Copyright 2000, CRC Press LLC, pp. V-1-51-9; Morrison et al., "Clinical Applications of Micro- and Nanoscale Biosensors" in Biomedical Nanostructures. Edited by K. E. Gonsalves, C. L. Laurencin, C. R. Halberstadt, L. S, Nair. 2008, John Wiley & Sons, Inc.; and U.S. Pat. No. 6,802,811, each of which is incorporated herein by reference.

The one or more sensors operably connected with the electronics module and/or programmable microprocessor can include, but are not limited to, one or more biosensors, chemical sensors, pressure sensors, temperature sensors, flow sensors, viscosity sensors, shear sensors (e.g., for measuring the effective shear modulus of the fluid at a frequency or strain-rate), pH sensors, optical sensors (e.g., charged couple device (CCD) array), optical waveguide sensors, acoustic sensors, surface acoustic wave sensors, quartz microbalance sensors, metal oxide sensors, bulk acoustic wave sensors, plate acoustic wave sensors, electrical sensors, magnetic sensors, interdigitated microelectrode sensors, electrochemical sensors, electrically conducting sensors, artificial noses, electronic noses, electronic tongues, semiconductive gas sensors, mass spectrometers, near infrared and infrared spectrometers, ultraviolet sensors, visible light-based sensors, fluorescence spectrophotometers, conductive-polymers, gas-fluorescence spectrophotometers, impedance spectrometers, aptamer-based biosensors, ion mobility spectrometry, photo-ionization detectors, amplifying fluorescent polymer sensors, ion mobility spectrometry, electrical impedance, microgravimetric sensors, cantilever and microcantilever sensors, accelerometers, global positioning devices, clocks or time-keeping devices. See, e.g., U.S. Pat. Nos. 5,522,394; 5,873,835; 6,409,674; 6,111,520; 6,278,379; 6,475,639; 6,802,811; 6,855,115, 6,517,482; 6,675,030; 6,836,678; 6,954,662; 7,184,810; 7,299,080, and U.S. Patent Application 2005/0277839, each of which is incorporated herein by reference.

The one or more sensors of the device can be configured to send data regarding a physiological condition in the subject to the programmable microprocessor of the device or to a electronics module operably connected to the programmable microprocessor. Conversely, the electronics module can be configured to instruct the one or more sensors to collect and transmit data or other information regarding one or more physiological conditions or indicators thereof at specified regular intervals and/or when triggered by sensed events or by initiation of particular device activity. The device may further include information storage. For example, measurement of one or more physiological condition may be collected and stored at specified times on a daily basis with an associated time stamp. More than one physiological condition may be measured simultaneously and associated with one another during processing. For example, measurement of temperature, or a localized temperature of an associated nerve tissue or circulatory tissue, can be assessed at the same time as measurement of blood glucose levels. A temperature measurement can also be triggered by other sensor activity such as when a measured exertion level reaches a specified limit value or immediately following caloric intake.

Detection

In some embodiments, the target area is identified by administering an imaging agent, such as a fluorescent dye, to a subject, which is then detected. In general, an imaging agent label provides a detectable signal. Non-limiting examples of labels useful in the invention include fluorescent dyes (e.g., fluorescein isothiocyanate, Texas red, rhodamine, and the like), enzymes (e.g., LacZ, CAT, horseradish peroxidase, alkaline phosphatase, I 2-galactosidase, .beta.-galactosidase, and glucose oxidase, acetylcholinesterase and others, commonly used as detectable enzymes), quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; magnetic particles; electrical labels; thermal labels; luminescent molecules; phosphorescent molecules; chemiluminescent molecules; fluorophores such as umbelliferone, fluorescein, rhodamine, tetramethyl rhodamine, eosin, green fluorescent protein, erythrosin, coumarin, methyl coumarin, pyrene, malachite green, stilbene, lucifer yellow, Cascade Blue®, dichlorotriazinylamine fluorescein, dansyl chloride, phycoerythrin, fluorescent lanthanide complexes such as those including Europium and Terbium, molecular beacons and fluorescent derivatives thereof, a luminescent material such as luminol; light scattering or plasmon resonant materials such as gold or silver particles or quantum dots; radiolabels or heavy isotopes including 14C, 1231, 1241, 1311, 1251, Tc99m, 32P, 35S or 3H; or spherical shells; and probes labeled with any other signal generating label known to those of skill in the art, as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland. Two or more different labels may be used together to detect two or more analytes in a single assay.

The User interface could include indicators, displays, buttons, touchscreens, head-mounted displays, and/or other elements configured to present information about the imaging system to a user and/or to allow the user to operate the imaging system. Additionally or alternatively, the imaging system could be configured to communicate with another system (e.g., a cellphone, a tablet, a computer, a remote server) and to present elements of a user interface using the remote system. The user interface could be disposed proximate to the light source, first camera, SLM, MD6, second camera, stage actuator, controller, or other elements of the imaging system or could be disposed away from other elements of the imaging system and could further be in wired or wireless communication with the other elements of the imaging system. The user interface could be configured to allow a user to specify some operation, function, or property of operation of the imaging system. The user interface could be configured to present an image of the target area generated by the imaging system or to present some other information to a user. Other configurations and methods of operation of a user interface are anticipated.

Communication system(s) may also be operated by instructions within the program instructions, such as instructions for sending and/or receiving information via a wireless antenna, which may be disposed on or in the imaging system. The communication system(s) can optionally include one or more oscillators, mixers, frequency injectors, etc. to modulate and/or demodulate information on a carrier frequency to be transmitted and/or received by the antenna. In some examples, the imaging system is configured to indicate an output from the controller (e.g., one or more images of the target area) by transmitting an electromagnetic or other wireless signal according to one or more wireless communications standards (e.g., Bluetooth, WiFi, IRdA, ZigBee, WiMAX, LTE). In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and so forth.

In various implementations, the described aspects may comprise part of a cellular communication system. Examples of cellular communication systems may include CDMA cellular radiotelephone communication systems, GSM cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (NAMPS) cellular radiotelephone systems, third generation (3G) systems such as WCDMA, CDMA-2000, UMTS cellular radiotelephone systems compliant with the Third-Generation Partnership Project (3GPP), and so forth.

In various aspects, the electronics module includes the functionality to wirelessly receive and/or wirelessly transmit data, e.g., physiologic data, to a computer, such as a mobile computer.

Further, in various aspects, the electronics module may incorporate and/or be associated with, e.g., communicate with, various devices. Such devices may generate, receive, and/or communicate data, e.g., physiologic data. The devices include, for example, "intelligent" devices such as cellular phones, personal data assistants, or devices configured to be used by a health care provider or a patient to receive or transmit data to and from the analyte devices.

The mobile computer may be implemented as a mobile telephone. For example, the mobile computer may be implemented as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

In some examples, the communication system(s) could include one or more wired communications interfaces and the imaging system could be configured to indicate an output from the controller by operating the one or more wired communications interfaces according to one or more wired communications standards (e.g., USB, FireWire®, Ethernet, RS-232). Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Vehicles of communication include a network. In various aspects, the network may comprise local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

The computer readable data storage may further contain other data or information, such as contain calibration data corresponding to a configuration of the imaging system, a calibration target, or some other information. Calibration, imaging, and/or other data may also be generated by a remote server and transmitted to the imaging system via communication system(s).

Other Uses

Acupuncture is an alternative medicine that treats patients by insertion and manipulation of needles in the body at selected points. See, Novak, Patricia D. et al (1995). Dorland's Pocket Medical Dictionary (25th ed.), Philadelphia: (W.B. Saunders Publisher), ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: www.acupuncturehealing.org/acupuncture-points-map.html, Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter(s) typically refers to a body organ, or other tissue location associated with, or affected by, that acupoint. However, usually only the letter(s), not the name of the body organ, is used in referring to the acupoint, but not always. Thus, for example, the acupoint SP4 is the same as acupoint Spleen 4 which is the same as SP-4 which is the same as SP 4 which is the same as Gongsun. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is WHO STANDARD ACUPUNCTURE POINT LOCATIONS IN THE WESTERN PACIFIC REGION, published by the World Health Organization (WHO), Western Pacific Region, 2008 (updated and reprinted 2009), ISBN 978 92 9061 248 7 (hereafter "WHO Standard Acupuncture Point Locations 2008"). The Table of Contents, Forward (page v-vi) and General Guidelines for Acupuncture Point Locations (pages 1-21), as well as pages 66, 71 and 199 (which illustrate with particularity the location of acupoints ST40, SP4 and LRB, respectively) are incorporated herein by reference. Moreover, the above-cited portions of the WHO Standard Acupuncture Point Locations 2008 reference book, with the exception of pages 66, 71 and 199, may be found as Appendix D in Applicant's earlier-filed patent application, U.S. patent application Ser. No. 13/622,497, filed Sep. 19, 2012, which application is incorporated herein by reference.

Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004-02-01 (www.acupuncturetoday.com/abc/electroacupuncture.php).

The invention provides for the devices and methods of the invention to be used for, for example, the placement of acupuncture needles or electroacupuncture needles.

While the invention has been described in detail and with reference to specific examples thereof, it will be apparent to one skilled in the art that various changes and modifications can be made therein without departing from the spirit and scope thereof.

What is claimed is:

1. A device for guiding the implanting of a sensor within the skin of a subject, the device comprising:
   a housing that is adapted for placement on the outer skin of the subject, said housing defining an area of the skin over which an ultraviolet illuminator and a camera are positioned in said housing at a predetermined distance above the area of the skin, and comprising:
   at least one insertion port contiguous with an insertion channel that is formed at a predetermined angle within said housing, said insertion channel having an opening that is adapted to rest against the skin;
   said ultraviolet illuminator illuminating a fluorescent material that is previously positioned within the reticular dermis of the subject that is located underneath said housing;
   said camera capturing an image of the skin, including the reticular dermis, located beneath said housing; and
   a display that permits a user to view said image when passing an applicator and/or sensor through said insertion port and down through said insertion channel and out of said opening such that a tip of said applicator and/or sensor is visible in said image and is positioned within the reticular dermis for delivering the applicator and/or sensor therein.

2. The device of claim 1 wherein said camera comprises a wireless transponder for communicating wirelessly with said display, said transponder providing said image to said display.

3. The device of claim 1 wherein the camera is a confocal microscope.

4. The device of claim 1 wherein the focal plane of the camera is adjusted via the display.

5. The device of claim 1 wherein the display is a smartphone.

* * * * *